US00PP19218P2

(12) United States Plant Patent
Hanes

(10) Patent No.: US PP19,218 P2
(45) Date of Patent: Sep. 16, 2008

(54) *PETUNIA* PLANT NAMED 'WHIP BRIINK'

(50) Latin Name: *Petunia hybrida*
Varietal Denomination: Whip Briink

(75) Inventor: Mitchell E. Hanes, Morgan Hill, CA (US)

(73) Assignee: Goldsmith Seeds, Inc., Gilroy, CA (US)

( * ) Notice: Subject to any disclaimer, the term of this patent is extended or adjusted under 35 U.S.C. 154(b) by 0 days.

(21) Appl. No.: 11/824,622

(22) Filed: Jul. 2, 2007

(51) Int. Cl.
*A01H 5/00* (2006.01)

(52) U.S. Cl. ..... Plt./356
(58) Field of Classification Search ..... Plt./356
See application file for complete search history.

(56) References Cited

U.S. PATENT DOCUMENTS

PP13,556 P2 * 2/2003 Sakazaki ..... Plt./356
PP14,325 P2 * 11/2003 Hanes ..... Plt./356

OTHER PUBLICATIONS

UPOV Rom GTITM Computer Database, GTI Jouve Retrieval Software 2007/4 Citation For 'Whip Briink'.*

* cited by examiner

*Primary Examiner*—Wendy C. Haas
(74) *Attorney, Agent, or Firm*—Jondle & Associates, P.C.

(57) ABSTRACT

A new *petunia* plant particularly distinguished by bright pink flowers, compact plant habit with vigorous growth, and an initially spreading, upright plant habit, is disclosed.

1 Drawing Sheet

Genus and species: *Petunia hybrida.*
Variety denomination: 'Whip Briink'.

BACKGROUND OF THE NEW PLANT

The present invention comprises a new and distinct cultivar of *petunia,* botanically known as a *Petunia hybrida,*and hereinafter referred to by the cultivar name 'Whip Briink'. The new cultivar originated from a hybridization made in August 2002 in Gilroy, Calif. The female parent was '1092-1', a pink-flowered proprietary *petunia* plant (unpatented), while the male parent was 'Conbloss', a white-flowered *petunia* plant (U.S. Plant Pat. No. 13,556). The seeds produced by the hybridization were sown in February 2003. A single plant selection was chosen for further evaluation and for asexual propagation in April 2003.

The new cultivar was created in 2002 in Gilroy, Calif. and has been asexually reproduced repeatedly by vegetative cuttings and tissue culture in Gilroy, Calif. and Andijk, The Netherlands over a three and a half year period. The plant has also been trialed at Gilroy, Calif., Hillscheid, Germany and Andijk, The Netherlands. The present invention has been found to retain its distinctive characteristics through successive asexual propagations.

Plant Breeder's Rights were applied for in Europe in November 2006.

SUMMARY OF THE INVENTION

The following are the most outstanding and distinguishing characteristics of this new cultivar when grown under normal horticultural practices in Gilroy, Calif. and Hillscheid, Germany.

1. Bright pink flowers;
2. Compact plant habit;
3. Vigorous growth; and
4. An initially spreading plant habit;

DESCRIPTION OF PHOTOGRAPHS

This new *petunia* plant is illustrated by the accompanying photographs which show the overall plant habit including blooms, buds, and foliage of the plant; the colors shown are as true as can be reasonably obtained by conventional photographic procedures. The photographs are of a 20-week old plant grown in a greenhouse in Hillscheid, Germany during the summer months.

Figure 1:
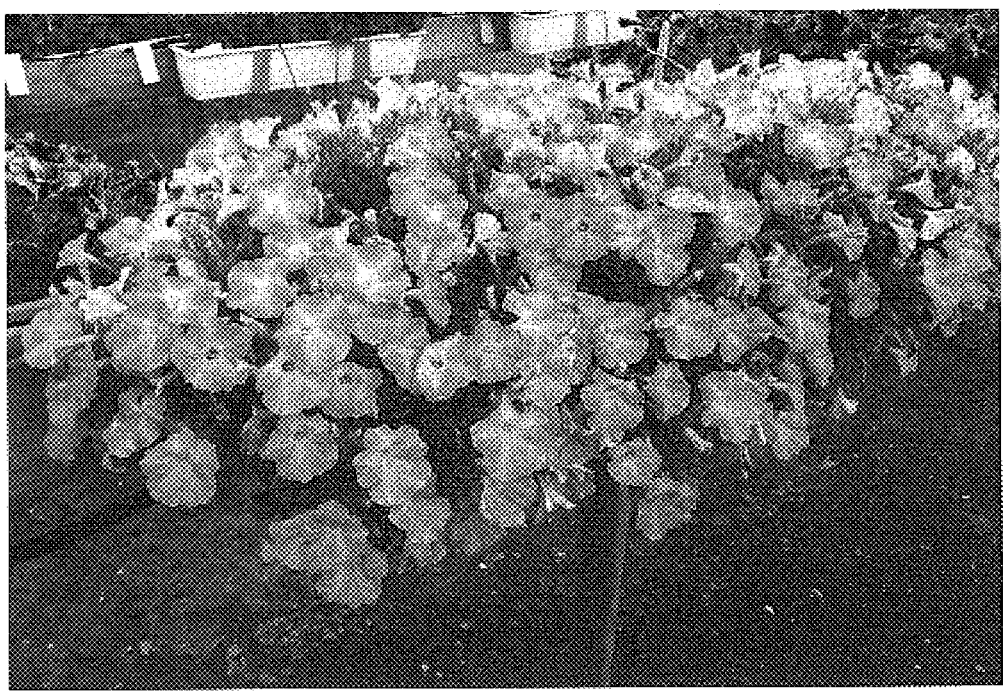
Figure 2:
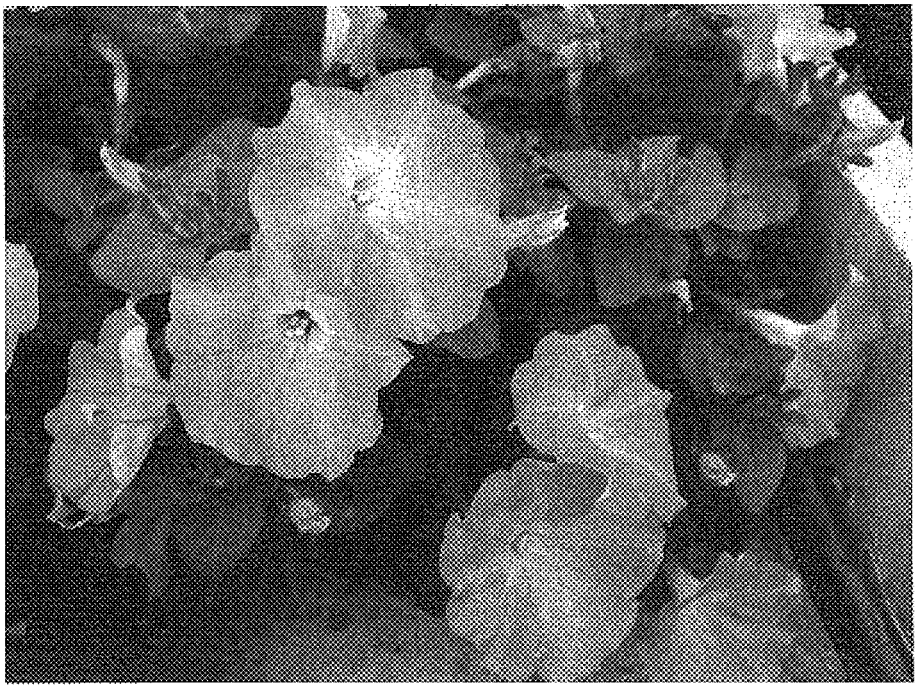

FIG. 1 shows the overall plant habit including blooms, buds, and foliage of the plant FIG. 2 shows a close-up of flowers of the plant.

DESCRIPTION OF THE NEW CULTIVAR

The following detailed description sets forth the distinctive characteristics of 'Whip Briink'. The data which define these characteristics were collected from asexual reproductions carried out in Gilroy, Calif. The plant history was taken on 12-to-15-week-old plants which were planted as rooted cuttings in 4-inch pots in the early spring in a greenhouse trial setting. The plants had one plant growth regulator treatment and one terminal pinch after cuttings were transplanted. Color readings were taken under natural light in the greenhouse in March. Color references are primarily to the RHS Colour Chart of The Royal Horticultural Society of London (R.H.S.) (2001). Texture description data was viewed with a dissecting microscope.

DETAILED BOTANICAL DESCRIPTION

Classification:
*Family.*—Solanaceae.
*Botanical.—Petunia hybrida.*
*Common name.—Petunia.*

Parentage:
*Female parent.*—'1092-1', a proprietary pink-flowered *petunia* plant (unpatented).

*Male parent.*—'Conbloss' (U.S. Plant Pat. No. 13,556), a white-flowered *petunia* plant.

Growth:

*Form.*—Herbaceous annual.

*Habit.*—Spreading initially and relatively upright plant habit; decumbent trailing plant habit later; pinching enhances branching; vigorously growing and well branched.

*Height* (*measured from the top of the soil*).—12.0 cm to 15.0 cm.

*Width* (*horizontal plant diameter*).—30.0 cm to 34.0 cm.

*Time to produce a finished flowering plant.*—Approximately 8 to 11 weeks for a 4-to-6 inch pot in the spring.

*Outdoor plant performance.*—Use in hanging baskets, mixed containers, and patio containers.

*Time to initiate and develop roots.*—18 to 25 days.

*Root description.*—White, fibrous.

Stems:

*Length.*—15.0 cm to 18.0 cm.

*Diameter.*—0.4 cm to 0.5 cm.

*Internode length.*—1.5 cm to 2.0 cm.

*Stem color.*—A little darker than RHS 144A.

*Anthocyanin.*—Absent.

*Texture.*—Glandular hairs of various sizes.

Leaves:

*Arrangement.*—Alternate; upper leaves subalternate.

*Size.*—Length: 4.0 cm to 6.0 cm. Width: 1.8 cm to 2.8 cm.

*Shape.*—Elliptical.

*Margin.*—Entire.

*Apex.*—Acute.

*Base.*—Attenuate.

*Color.*—Immature: Upper surface: RHS 137B to RHS 137C. Lower surface: Closest to RHS 138B. Mature: Upper surface: RHS 138A. Lower surface: Closest to RHS 138B.

*Texture.*—Short glandular hairs.

*Venation.*—Pinnate.

*Venation color.*—RHS 144A.

*Petioles.*—Length: 1.0 cm. Width: 0.3 cm. Color: RHS 144A. Texture: Glandular hairs of various sizes.

Flower bud:

*Shape.*—Oblong.

*Size.*—Length: 2.6 cm to 3.5 cm. Diameter: 0.5 cm to 0.6 cm.

*Color* (*when cold; just starting to show*).—Lighter than RHS N57D.

Inflorescence:

*Blooming habit.*—Continuous throughout the growing season; good floriferousness.

*Inflorescence type.*—Flowers appear solitary in upper leaf axis.

*Floret type.*—Funnel-shaped; 5 lobed petals; fused at the base; calyx, 5 deeply lobed sepals.

*Number of flowers per node.*—1.

*Lastingness of individual blooms on the plant.*—4 to 8 days.

*Fragrance.*—Slightly sweet.

*Pedicels.*—Color: RHS 144A. Length: 3.8 cm to 4.2 cm. Diameter: 0.2 cm. Texture: Glandular hairs of various sizes.

Flowers:

*Shape.*—Funnel-shaped, formed by 5 fused petals.

*Immature.*—Diameter: 4.5 cm. Color: Upper surface: RHS N74B with mid-veins a soft hue of RHS 164C and veins of RHS 144B. Lower surface: RHS 75C.

*Mature flower.*—Diameter: 5.5 cm to 6.0 cm. Depth: 5.0 cm to 5.5 cm. Color: Upper surface: Between RHS N74B and RHS N74C with mid-veins a soft hue of RHS 146C and veins of RHS 144B. Lower surface: RHS 75C.

*Corolla tube.*—Length: 2.5 cm. Color inside (throat): Closest to RHS 155C with veins of RHS 144B. Color outside: Closest to and between RHS 149D and RHS 150D. Texture: Glandular hairs of various sizes.

*Petals.*—Apex: Mucronate. Base: Fused. Margin: Entire. Waviness: Moderately wavy. Lobation: Slight to moderate. Texture: Papilose.

*Calyx.*—5 deeply lobed sepals, fused at the base.

*Sepals*—Number: 5. Color: RHS 137B. Length: 1.7 cm to 1.8 cm. Width: 0.3 cm to 0.4 cm. Shape: Oblong to oblanceolate. Apex: Acute. Base: Fused. Margin: Entire. Texture: Glandular hairs of various sizes.

Reproductive organs:

*Stamens.*—Number: 5, 2 tall, 3 short. Filament color: RHS 155C. Filament length: 1.7 cm to 2.3 cm. Filament diameter: 0.1 cm. Pollen color: RHS 11B. Pollen amount: Moderate.

*Pistil.*—Number: 1. Length: 1.6 cm. Diameter: 0.1 cm. Stigma color: RHS 144A. Style color: RHS 133C.

Fruit and seed set: No seed set observed so far.

Disease and insect resistance: No particular resistance or susceptibility has been observed.

COMPARISON WITH PARENTAL AND COMMERCIAL CULTIVARS

'Whip Briink' differs from the female parent '1092-1' (unpatented) by having a brighter pink flower color and smaller leaves than '1092-1'. Additionally, 'Whip Briink' has a more compact plant habit and better vigor than '1092-1'.

'Whip Briink' differs from the male parent 'Conbloss' (U.S. Plant Pat. No. 13,556) by having a bright pink flower color, while 'Conbloss' has a white flower color. Additionally, 'Whip Briink' has lighter green foliage, a longer petiole, larger flower diameter and a brighter yellow pollen color than 'Conbloss'.

'Whip Briink' differs from the commercial variety 'Jam Hopink' (U.S. Plant Pat. No. 14,325) by having lighter green and smaller foliage than 'Jam Hopink'. Additionally, 'Whip Briink' has a more compact plant habit with more branching, a smaller flower size and a lighter colored pink flower than 'Jam Hopink'.

I claim:

1. A new and distinct cultivar of *petunia* plant as shown and described herein.

* * * * *